(12) United States Patent
Muller et al.

(10) Patent No.: US 6,480,566 B2
(45) Date of Patent: Nov. 12, 2002

(54) METHOD AND APPARATUS FOR MAMMOGRAPHY

(75) Inventors: Serge Muller, Guyancourt (FR); Andreas Rick, Plaisir (FR); Jean-Pierre Saladin, Bagneux (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/007,810

(22) Filed: Nov. 9, 2001

(65) Prior Publication Data

US 2002/0090052 A1 Jul. 11, 2002

(30) Foreign Application Priority Data

Nov. 23, 2000 (FR) .............................................. 00 15129

(51) Int. Cl.⁷ .................................................. A61B 6/04
(52) U.S. Cl. ......................................................... 378/37
(58) Field of Search ............................................ 378/37

(56) References Cited

U.S. PATENT DOCUMENTS 5,596,620 A    1/1997   Canistraro et al. ............ 378/84

FOREIGN PATENT DOCUMENTS

| EP | 0332519 | 9/1989 |
| EP | 0483005 | 4/1992 |
| WO | 0065989 | 11/2000 |

Primary Examiner—Craig E. Church
(74) Attorney, Agent, or Firm—Jay L. Chaskin

(57) ABSTRACT

Method and apparatus for medical radiology and, in particular, galactography in the field of mammography. The method of obtaining radiological images in galactography comprises acquiring of a first radiological image of the breast in a compressed state: introducing a contrast medium in a part of the breast; acquiring at least a second radiological image of the breast in the compressed state and with contrast medium; and partial or complete subtraction of the first image in relation to the second image, or vice versa. An apparatus for use of the method comprises means for maintaining a breast compressed or immobilized and means for holding a catheter or the like for introducing a contrast medium in the breast.

40 Claims, 4 Drawing Sheets

METHOD AND APPARATUS FOR MAMMOGRAPHY

CROSS REFERENCE TO RELATED APPLICATIONS

This application claims the benefit of a priority under 35 USC 119 to French Patent Application No. 0015129 filed Nov. 23, 2000, the entire contents of which are incorporated by reference.

BACKGROUND OF THE INVENTION

The present invention concerns medical radiology and, in particular, the galactography technique in mammography.

Mammography is an imaging technique used, notably, for the detection of breast cancers. It involves an examination which is the first among three stages of medical follow-up, namely: detection, for example, of a breast cancer; diagnosis; and intervention.

Detection covers women typically in the age bracket of 40 or 50 to 70 years old. At the examination, films are taken at two different angles: one so-called craniocaudal front view, that is, in the direction from head to toe, and a mediolateral oblique (MLO) view. In the latter case, the detector is situated under the axillary space. A film is then taken of the entire mammary gland, of the axillary space and of the whole length of the breast.

The internal structure of the breast comprises fibrous tissues and adipose tissues, which contain fat. The mammary gland has a structure which resembles a natural sponge. The mass of that sponge comprises the fibrous tissues, the fat being located inside the cells of the sponge. When a projection image is made, which is the case in radiology, it is sought to obtain an image giving the most contrast between those two types of tissue. That normal structure of the breast and possibly so-called superdensity areas, generally associated with lesions which can be either cancerous or benign, are visualized. It is therefore sought to mark those areas and to characterize them in order to determine their nature.

It is also sought to detect small calcium deposits. When they are of very small size, that is, between 100 microns and 1 millimeter, it is a question of microcalcifications. If it is felt that those calcifications might possibly be malignant, the patient passes from the detection stage to the diagnostic stage. Additional views and geometric enlargements are then made to refine the radiological analysis. Some of the characteristics (density, shape) are used in order to have greater certainty as to the malignant or benign character of the site.

These analyses can be accompanied by a clinical examination (palpation of the breast, etc.).

Upon the interventional stage, several procedures are open, particularly a needle puncture on the area which seems suspicious. This protocol is often prompted by observation of an opacity or of a microcalcification.

In some cases, a nipple discharge occurs. It is then important to study the structure behind the nipple. In addition to adipose and fibrous tissues, there is an arborescent network of ducts called galactophores, which bring the milk to the nipples. The endings of those ducts at the nipple, called galactophorous orifices, typically number fifteen to twenty. When there is a nipple discharge, the galactophorous orifice at the source thereof is marked and the duct concerned is visualized by a so-called galactography technique.

Up to now, galactography has been carried out solely with images on standard X-ray film. The technique consists of dilating the galactophorous orifice with a needle or a plastic cannula. Once the orifice is sufficiently dilated, an X-ray attenuating contrast medium is injected by that needle or cannula.

The galactophorous orifice is then closed by a wax-base plug. The breast is compressed by means of a compression plate and a radiological image is made of the entire breast. That makes it possible to see the galactophorous network which has been injected.

The examination can thus be summed up in the following stages: i) beginning with the uncompressed breast, ii) dilation of the galactophorous orifice, iii) injection of contrast medium, iv) closing of the orifice, and v) compression of the breast on the film.

By analyzing those structures, some lesions can be marked, for example, galactophorous ducts which are intersected, dilated or otherwise approached, and pathologies situated inside the galactophorous ducts can thus be detected.

With this technique, a problem arises when the breast is very dense, so that the galactophorous ducts are hardly visible, even with injection of a contrast medium.

Furthermore, when a film is used, a good contrast (that is, good information legibility) requires the density of the X-ray flux reaching the film to come within a lower limit and an upper limit. As a result, the image can be saturated if the breast is dense and, therefore, does not offer good visibility of the galactophorous ducts.

Similar difficulties are also encountered in other aspects of mammography.

BRIEF DESCRIPTION OF THE INVENTION

In light of these problems, the invention proposes a mammography approach which takes advantage of techniques of digital processing of the radiological image in order to improve information legibility.

According to an embodiment the invention concerns a method of obtaining mammo-graphic images intended for galactography comprising the following stages:

a. acquiring a first radiological image of the breast in a compressed or immobilized state;

b. introducing a contrast medium in a part of the breast;

c. acquiring at least a second radiological image of the breast in the compressed or immobilized state and with contrast medium; and d. partial or complete subtraction of the first image in relation to the second image, or vice versa.

It is observed that, depending on the application of the invention and, notably, the radiation energies used, just holding the breast during the procedure can actually be envisaged, without having to compress it, or compressing it only slightly.

The first and second radiological images are advantageously obtained by means of a digital X-ray detector.

The contrast medium can be introduced in at least one galactophorous duct by injection in the nipple via at least one galactophorous duct. The contrast medium is preferably introduced when the breast is in the compressed or immobilized state. In a preferred embodiment, the contrast medium is introduced by a catheter or the like, which can be maintained in an adjustable position along at least one of the following axes: a lateral axis x in the patient's right-left direction; a lateral axis y in the costal grid-nipple direction; and an axis z in the direction of the thickness of the breast and preferably on both lateral axes x and y and axis z. The catheter or the like can be further adjustable in polar orientation. It can also be arranged to synchronize the movement of the catheter or the like along axis z, in the direction of the thickness of the breast, with the movement of compression of the breast.

The subtraction is advantageously of logarithmic type. Furthermore, a weighting factor can be applied to at least one among the first and second images and so as to obtain controlled visibility of the tissues superposed on the opacified parts. At least one of the weighting factors can be modified in real time in order to change the relative contrast of the opacified part of the breast and, notably, the galactophorous ducts and neighboring tissues.

With the method, at least one image can be acquired during introduction of the contrast medium in order to obtain information concerning the dynamics of progression of the contrast medium in the breast and, notably, in the galactophorous network.

The method can further include a stage of resetting of the first and second images before the subtraction, for example, by means of an "elastic" resetting algorithm.

In a customary application of the invention, the radiological images are obtained with X-rays presenting a maximum number of photons with an energy around 20 keV, which favors contrast of the breast tissues. However, in order to obtain better visibility of the contrast medium, iodinated, for example, an X-ray beam can be used advantageously with a spectrum of higher energy, for example, with a maximum number of photons around 35 keV.

According to an embodiment of the invention concerns an apparatus specifically adapted for obtaining mammographic images, intended for galactography, comprising combined in one unit: means for maintaining a breast compressed or immobilized; and means for holding a catheter or the like for introducing a contrast medium in the breast.

The means for holding is arranged to permit adjustable positioning of the catheter or the like along at least one among the aforesaid three axes x, y and z and preferably the set of both lateral axes x and y and axis z. The apparatus can include means of adjustment of the catheter or the like on a polar orientation. The means for holding can include means for grasping the catheter or the like by clipping or clamping. In the preferred embodiment, the means for grasping are guided in direction z of compression of the breast in a block mounted moving on two axes x and y in a lateral plane. If need be, the means for grasping can be arranged for positioning to be adjustable by motor drive for at least one of the axes x, y and z. The apparatus can further include means for synchronization of movement of the catheter or the like in the direction of compression of the breast with the movement of compression of the breast. The means for holding a catheter or the like are advantageously configured to make possible the introduction of the latter in a galactophorous orifice of the breast before compression of the breast and to keep the catheter in that orifice during compression of the breast. A housing can be provided for a digital X-ray detector positioned directly under the breast.

According to a third embodiment of the invention concerns a mammography system intended for galactography, comprising the apparatus, the latter being set up on the axis of emission of an X-ray source, a digital X-ray detector and its means for control, and means for processing the images obtained by the latter.

The means for image processing advantageously includes means for a subtraction of images taken, on the one hand, before and, on the other, during and/or after introduction of the contrast medium. The means for image processing can further include means for image resetting used in subtraction.

An embodiment of the invention also concerns the use of the aforesaid system for digital galactography by image subtraction.

BRIEF DESCRIPTION OF THE DRAWINGS

Other advantages and characteristics of the invention will be more clearly apparent on reading the preferred embodiments, given purely by way of nonlimitative example, with reference to the attached drawings in which:

FIG. 3b is a profile view of a element for clipping on the catheter of the device of FIG. 3a;

DETAILED DESCRIPTION OF THE INVENTION

Figure 1:
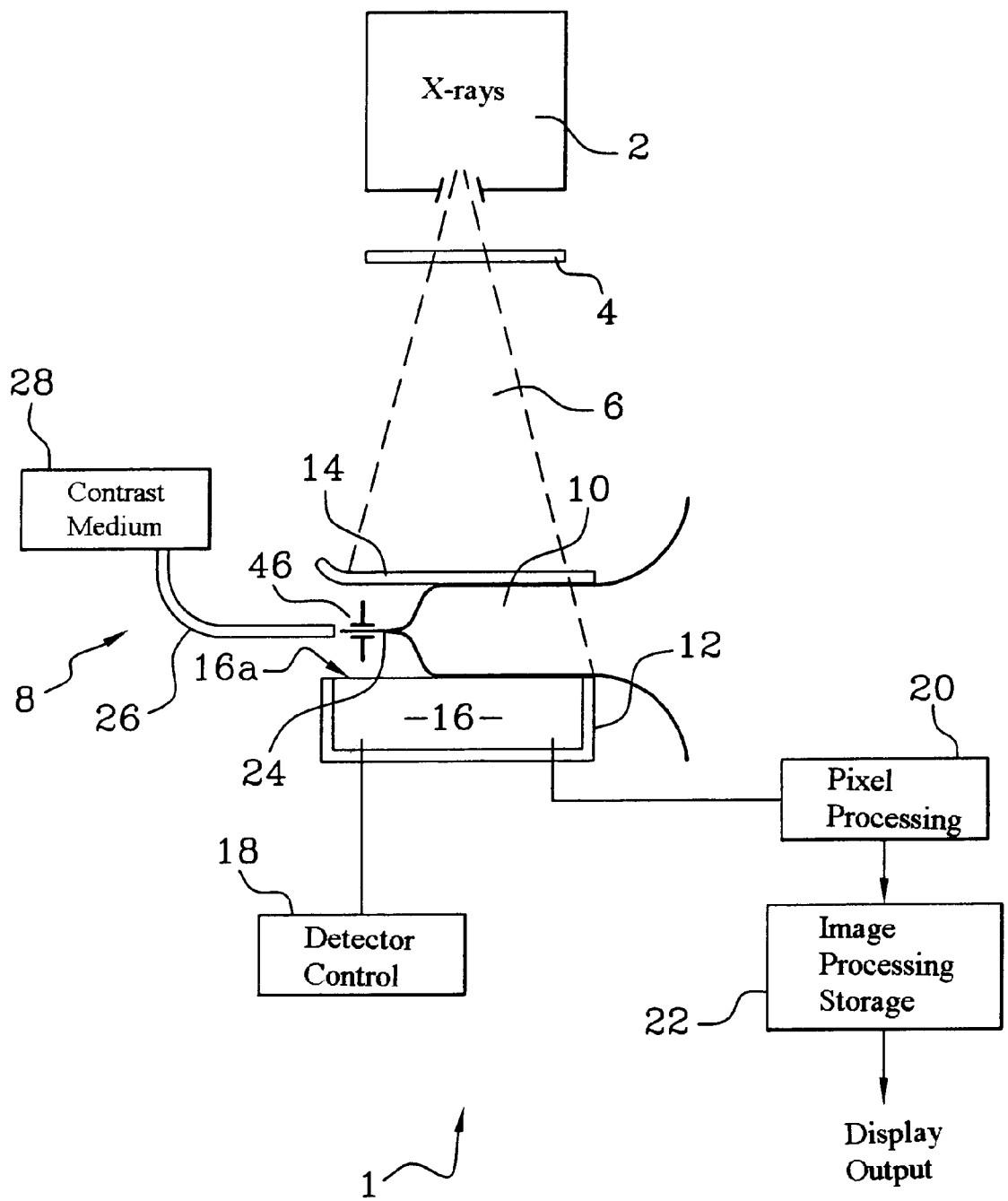
FIG. 1 is a simplified functional diagram of a mammography unit of an embodiment of the invention.

FIG. 1 shows schematically the basic elements used in a radiological imaging chain 1 for mammography according to an embodiment of the invention. A generator and an X-ray source 2 are provided, connected to a filter 4. The latter serves, notably, to eliminate low energy rays, which are useless and harmful to the patient, and makes it possible to transmit an appreciably monoenergetic X-ray beam 6.

The beam 6 coming from the filter 4 is directed toward a frame 8 intended to keep a breast 10 in a slightly compressed state. For that purpose, the frame 8 contains a lower block 12 on which the lower part of the breast rests, and an upper plate 14, called compression plate, which is movable in order to bear on the upper part of the breast and to compress it against the lower block. The movement of the plate can be motor-driven under control of an automatic or semiautomatic system. The lower block 12 integrates a digital X-ray detector 16, the sensitive surface 16a of which is turned toward the beam 6, directly under the breast.

The detector 16, made, for example, by solid state technology, replaces the standard radiological film used. Its design and method of operation are well known and will not be described here for the sake of conciseness. It is recalled that its sensitive surface 16a is composed of a two-dimensional matrix of X-ray sensitive elements. Each element supplies a signal according to a radiation dose received during a period of exposure. That signal, which corresponds to a pixel, is read on the set of elements of the matrix in order to reconstitute a radiological image in electronic form.

The different sequencing and control signals of the detector 16 are supplied by a control unit 18 which makes it possible, notably, to control exposure times and conditions. The output pixels of the detector are subjected to an initial processing (block 20) in order to adjust the signal levels, correct possible pixel defects and order them to deliver an electronic image according to a pre-established standard.

The images thus obtained are then processed in a unit 22 in order to make various conversions aimed at improving information legibility. Among those functions is digital subtraction imaging, which consists of removing or attenuating the common parts of two images in order to bring out the distinctive part, as will be described in detail below.

To make digital subtraction mammography possible according to the invention, the frame 8 includes a device for contrast medium injection in the breast, in order to obtain images taken before and after introduction of the contrast medium. This device contains a needle or a catheter, or even an injection cannula 24 intended to be inserted in a galactophorous orifice and connected by a flexible conduit 26 to a contrast medium injection source 28. A hollow needle with a diameter of around 1 mm can be used as catheter, as well as other instruments used in standard galactography for contrast medium injection.

Figure 2A:
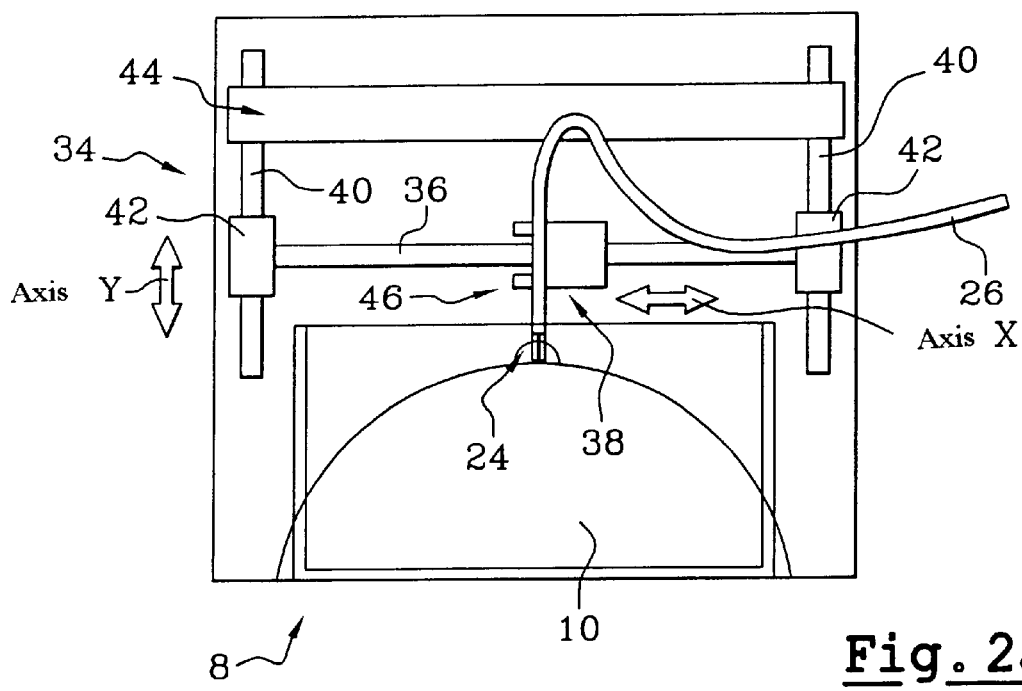
FIG. 2a is a plan view of a frame for breast compression and catheter positioning of an embodiment of the invention.
Figure 2B:
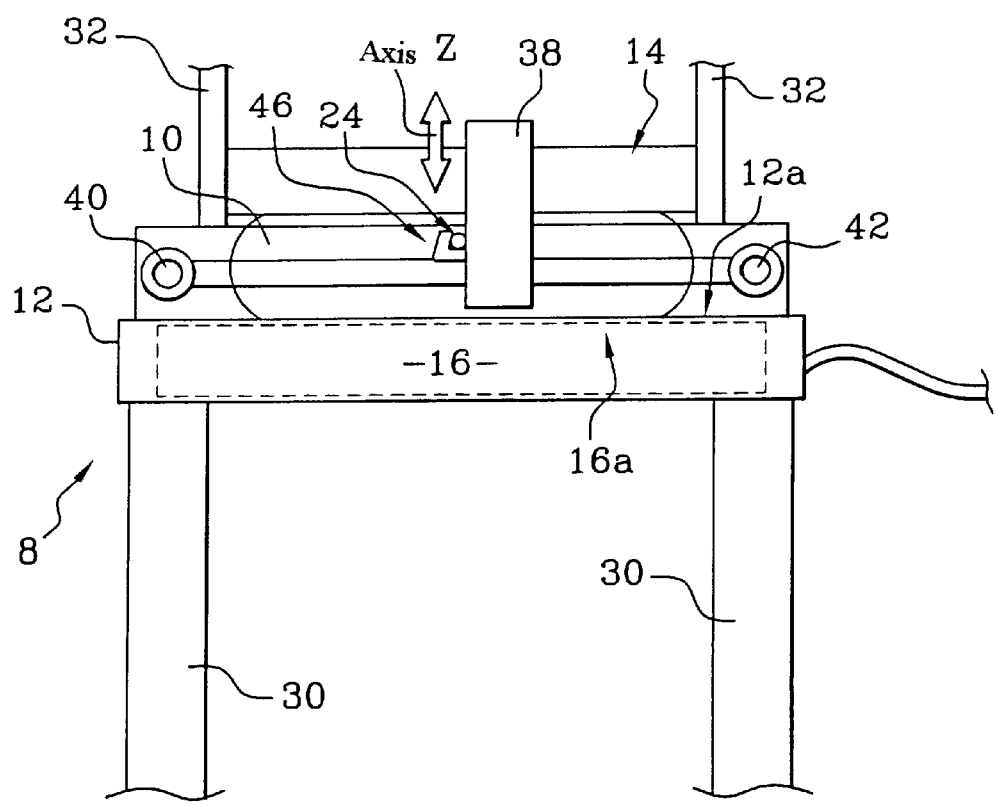
FIG. 2b is a front view of the frame of FIG. 2b.

FIGS. 2a and 2b illustrate the frame 8 in greater detail with plan and front views respectively. The frame 8 contains a bearing structure 30, at the base of which the lower block 12 is situated. This block presents a platform 12a on which the breast 10 rests (FIG. 2b) and includes the digital detector 16, so that the sensitive surface 16a of the latter is situated just below the platform 12a. The compression plate 14 is mounted sliding on uprights 32 to allow a controlled compression of the breast either by manual displacement or by electromechanical control.

The contrast medium injection apparatus contains a structure 34 which keeps the catheter 24 mobile on three perpendicular axes, so as to permit the adjustment of its positioning in a lateral plane (parallel to the platform 12a) and vertical plane. More precisely, the structure 34 allows a displacement of the catheter 24: (a) on a lateral axis in the right-left direction of the patient, making possible an adjustment of position when the breast is placed with a slight rotary motion on the platform 12a, or when it is desired to place the breast a little on the side of the detector 16, in the case of small breasts. That degree of freedom is materialized by one or more first rods 36 on axis x, on which a device 38 holding the catheter 24 is mounted sliding, the latter being laterally aligned perpendicular to axis x; (b) on a lateral axis y and in the costal grid-nipple direction (that is, on the axis of the catheter), in order to be adapted to the depth of the breast. This degree of freedom is materialized by a pair of second rods 40 perpendicular to the first rods 36 and to each end of the latter. On each second rod 40 a slide 42 is mounted, on which a respective end of the first rod or rods 36 is fastened, so that the latter can slide along the second rods on axis y. The second rods 40 are connected to the rest of the frame by a cross-beam 44; and (c) on an axis z at right angles to the detector (vertical) making possible an adaptation to the thickness of the compressed breast, typically from 2 to 10 cm, the patient generally standing or sitting for this type of examination. This degree of freedom is materialized by a slide in the device 38 holding the catheter 24, aligned with axis z and on which a catheter-fastening clamp or a clip 46 can be moved.

Figure 3A:
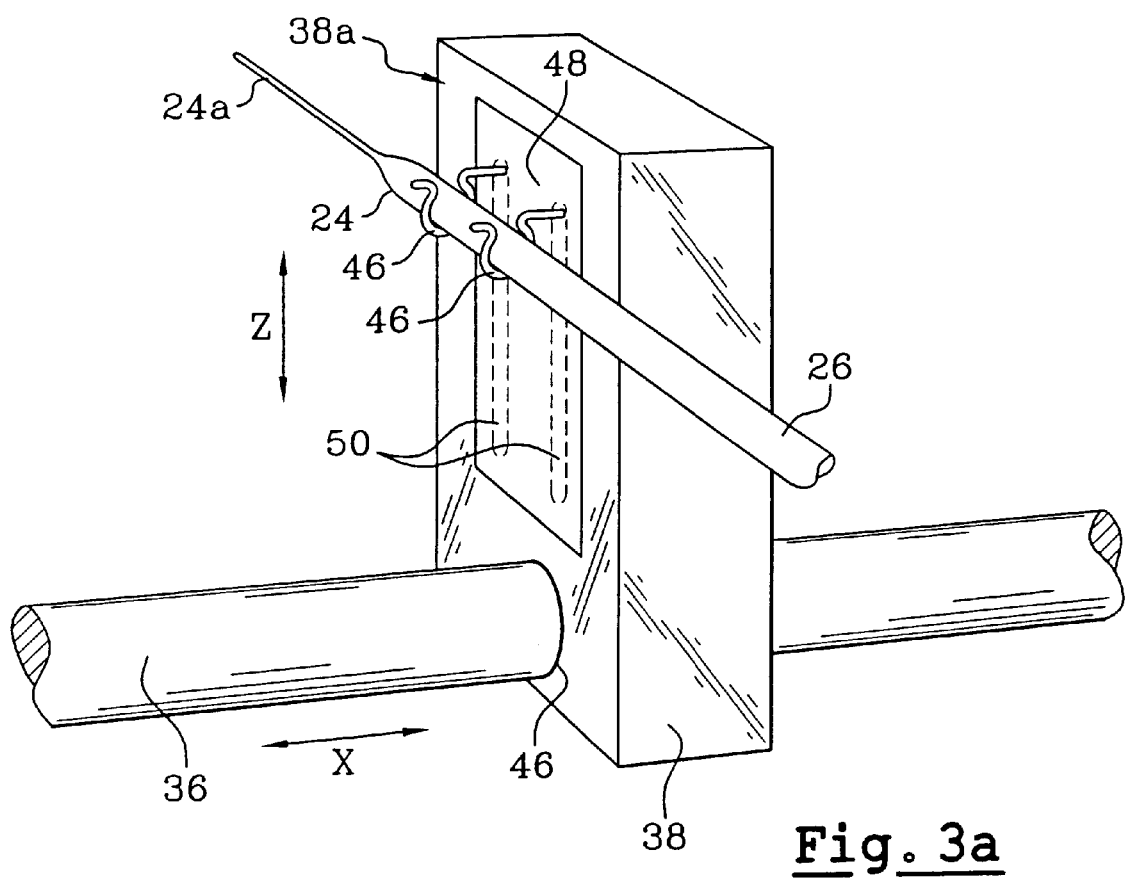
FIG. 3a is a general view of a device for holding the catheter in the frame of FIGS. 2a and 2b.
Figure 3B:
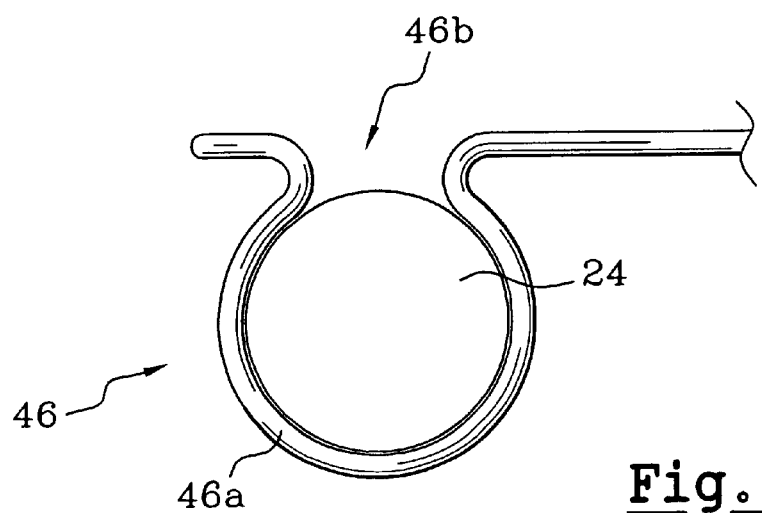

FIGS. 3a and 3b are more detailed views of the catheter holding device 38. It comes in the form of a block 38 having one or more holes 46 at the bottom, each crossed by a respective first rod 36 to enable a controlled slide along the axis x. One of the main faces 38a of the block contains a window 48 giving access to a pair of parallel slides 50, aligned along the vertical axis z. An element 46 for fastening the catheter 24 hangs from each slide. Each fastening element can thus be moved along its respective slide on axis z. In the example, the fastening element 46 contains a housing of circular section 46a configured to follow and hug the contour of the section of the catheter intended to be held.

The top of the housing has a flared open part 46b making it possible to introduce and withdraw the catheter by clipping and unclipping, the width of the opening being less than the diameter of the held section of the catheter 24. This type of fastening by clipping makes possible a rapid disengagement of the catheter in case of accident.

The material for the fastening element 46 is chosen for its elasticity and tolerance to sterilization treatment by autoclave or by decontamination agents commonly used in clinical practice.

The tip 24a of the catheter is sufficiently disengaged from the holding device 38 for the latter not to disturb the patient's movements.

Figure 4:
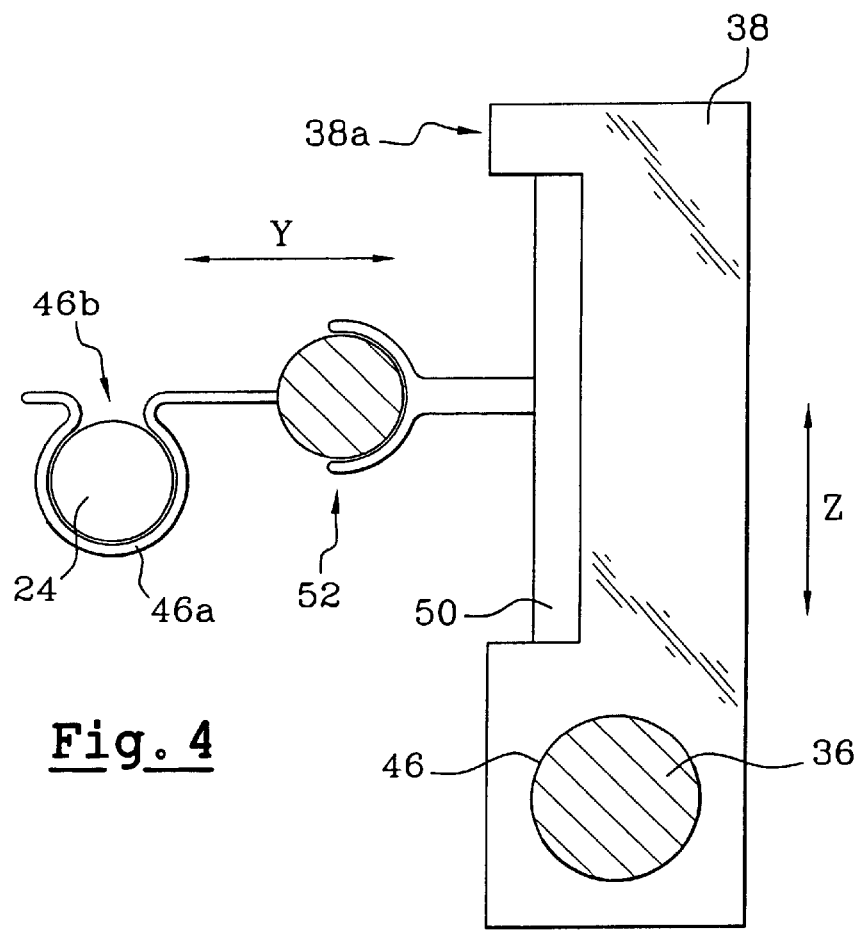
FIG. 4 is a side view of a catheter holding device allowing a polar adjustment of orientation of the latter, according to a variant of an embodiment of the invention.

According to an embodiment illustrated in FIG. 4, the fastening element 46 is attached to the slide 50 of the block 38 via a ball joint 52. This arrangement makes it possible to impart a polar adjustment motion by rotation of the fastening element and, therefore, of the catheter 24 for better control of positioning with respect to the nipple. The polar degree of freedom thus allowed is advantageous in order to compensate for a position of the breast slightly in rotation. For greater ease of rotary motion, a single holding element 46 can be provided in the slide 50 rather than a pair of such elements.

It is observed that one of the functions of the holding device 38 is to prevent the catheter 24 from being disengaged from the nipple under the effect of pressure upon injection of the contrast medium or upon an untimely contact between the patient or the operator and the catheter during an examination. The risks of injury or pain are thus minimized.

If the attachment entails a clamping of the catheter, one must make sure that this does not cause too great a narrowing of the passage, in order not to disturb the flow of product upon injection. The contrast medium injection device is designed to block any undesirable reflux after injection, for example, by means of a manual or automatic control valve. This arrangement makes it possible to keep the catheter 24 in place after injection and, notably, while the film is being taken with the presence of contrast medium. The plug of the galactophorous orifice is thus advantageously replaced by wax or the like.

It is, of course, possible to arrange for motor drive of all or some of the positioning movements along axes x, y and z according to various semi-manual or automatic control methods.

Motor drive can be of particular interest in movement along axis z (which corresponds to the direction of compression of the breast), for it makes it possible to synchronize the movement of the compression plate 14 or subject it to the adjustment movement along axis z of the catheter 24 (or vice versa), so that the catheter descends at the same time as the breast is compressed.

An example will now be described of use of the mammography chain 1 for a galactography examination by an image subtraction technique. In that application, the image subtraction technique is different from that previously used in angiography, in the sense that it is necessary to compress the breast.

An image subtraction must be carried out in place, that is, it is necessary to make one image before injection and another after injection, with the breast compressed for each of the two images. The use of a solid state digital detector 16 makes it possible in that case to obtain images with contrast media of iodinated type and with an acceleration voltage in the X-ray tube 2 higher than in standard mammography techniques, that is, with a greater energy spectrum. This is of great importance in increasing the contrast of the structures injected and if reducing the dose delivered to the patient. The possibility of delivering less of a dose also enables images to be made at identical doses for the examination of thicker breasts. This makes it possible to compress the breast less. Injecting the contrast medium when the breast is less compressed can therefore be envisaged.

Initially, the nipple is dilated, a cannula or a catheter 24 is placed in one of the galactophorous duct orifices and the breast is compressed with the plate 14. The compression is sufficient for the patient not to move during the examination in order to avoid a blurred image, but not too much, so as to let the contrast medium circulate. The holding device 38 serves to maintain the catheter firmly in the position adjusted along axes x, y, z and thus prevent the catheter from falling during the filming time. The nipple can be slightly off center, which requires an adjustment adapted to the volume of the breast and its positioning according to the patient's size and height in order to take variations of breast thickness into account. These adjustments are made thanks to the three axes of freedom x, y and z allowed by the frame 8, as explained above, ensuring an adaptation of positioning of the cannula or catheter to the anatomy. Once the cannula or catheter 24 is in place in the nipple, the image acquisition can be undertaken, first without contrast medium and then after injection.

After the two images are obtained, assuming that there has been no movement, a subtraction can be made, which will advantageously be of logarithmic type. This approach is based on the following considerations. The material analyzed is characterized by two parameters: its thickness and its linear attenuation coefficient. If there are N0 X photons reaching an elementary portion of material on input, there are N photons on output, with a number $\Delta N$ of photons absorbed in that portion of material. This number $\Delta N$ is proportional to the absorption coefficient $\mu$ of the material (the more attenuating the material, the more it is going to absorb photons), to the thickness 1 (the thicker the material, the more it absorbs radiation) and to the number of photons.

The following condition is therefore obtained:

$$\Delta N = -\mu . \Delta 1 . N \quad \text{(equation 1)}.$$

The "−" sign is explained by the fact that there is a reduction in number of photons.

By integrating on the entire thickness, the following condition is obtained:

$$N = N0 . \exp(-\mu . 1) \quad \text{(equation 2)}$$

If the material is not homogeneous, but contains several compounds which are going to vary with the location following a function $\mu$ (x,y,z), the term $\mu \Delta .1$ is replaced by the integral on the thickness L of function $\mu$ (x,y,z) d1, which gives $$N = N0 . \exp - \int \mu(x,y,z) . d1 \quad \text{(equation 3)}$$

This is the general equation, taking as hypothesis a monochromatic radiation corresponding to a single energy.

In order to do the subtraction, two images are used: one so-called "mask" image, which is the one obtained before injection of contrast medium, and an opacified image, after having sent the contrast medium. Typically, everything visible in the mask image must be visible in the opacified image, except for the elements which are superposed due to injection of the contrast medium. Considering a common point of the image (same coordinates x, y), an intensity expressed in number of photons is seen on the mask image:

$$I = I0 . \exp - \int \mu . d1 \quad \text{(equation 4)}$$

For the opacified image, the same thing is obtained, except that possibly the $\mu$ factor is going to change (becoming $\mu'$) by reason of the presence of the contrast medium, giving an intensity:

$$I' = I0 . \exp - \int \mu' . d1 \quad \text{(equation 5)}$$

If placed in a portion devoid of opacification, the coefficients $\mu$ and $\mu'$ will be identical in both images. If placed on a point where there is actually an opacification (in the opacified image), the coefficient $\mu'$ will be different. What is of interest here is the integral of $\mu$.d1 and, in particular, the integral of the difference in coefficients $\mu$ and $\mu'$ of both images. If placed on the galactophorous duct which has been opacified, there is a difference between coefficients $\mu$ and $\mu'$.

To be able to demonstrate that, the subtraction of I and I' (equation 5–equation 4) is performed. However, there is not direct access to the integral of the coefficient, but only to the exponential of the integral. To be able to access the integral, the logarithm of the expression I0/I is taken, which is equal to $\int \mu$.d1 for the mask image. The logarithm of the expression I0/I' is likewise taken for the opacified image, equal to $\int \mu$.d1. If the logarithmic subtraction is made, one obtains:

$$\Delta Ln = \int (\mu - \mu') d1 \quad \text{(equation 6)}$$

where Ln signifies the base logarithm e. This corresponds to the base logarithmic subtraction.

Only the opacified part of the image then remains, namely, the galactophorous network injected. Sometimes the practitioner prefers to increase the visibility of the galactophorous ducts, while preserving the visibility of the neighboring structure so that it can be marked in space. In that case, instead of making a logarithmic subtraction, which corresponds simply to the difference of the two terms, a part of the mask image is added in order to increase the contrast just on the opacified part. For that purpose, weighting factors are added on each of the two image intensities I and I', which gives the following general expression for image intensity Is at an elementary point after subtraction:

$$Is = \alpha . Ln(I') - \beta . Ln(I) \quad \text{(equation 7)}$$

where: $\alpha$ is the weighting factor of the opacified image, and $\beta$ is the weighting factor of the mask image.

In general, $\alpha = \beta = 1$. If $\alpha = 1$ is fixed, the visibility of the tissues superposed on the opacified ducts can be progressively varied by increasing $\beta$ from 0 to 1. The values of $\alpha$ and $\beta$ can be modified in real time in order to change the relative contrasts of the opacified ducts and surrounding tissues.

Logarithmic subtraction constitutes the first step.

A second step takes into account the fact that the area scanned can. in practice, not remain immobile between the two images. It is therefore sometimes necessary to reset one image on the other, in order to take into account the possible movements of the patient between the acquisitions of the mask image and opacified image. For that purpose, so-called "elastic" reset algorithms can be used, that is, aimed at evaluating the conversion of one image to the other, assuming that the parts imaged can move according to a model which is not rigid. However, it is based on the hypothesis that the movements are not too abrupt, which is the case in nature.

As for the radiological parameters adapted to subtraction techniques in mammography with an electronic detector, according to the invention, the linear attenuation coefficients are analyzed as a function of the energy of the X-rays sent. The maximum contrast is then established with a given X-ray energy. That energy is chosen as a function of the material it is necessary to differentiate in the object studied. In mammography the tissues are soft and of different kinds: fibers and adipose tissues (fat). Fat attenuates the X-rays less than the fibrous tissues. The applicant determined that good results are obtained when the spectrum of the X-rays transmitted presents a maximum of photons with an energy situated at around 20 keV, in the form of a line characteristic of that energy. The ideal monoenergetic beam which would give the maximum contrast is then approached.

That line can be produced with an X-ray tube, the path of which is made of a given material, combined with a filter. It is recalled that the path is the emitting surface of a rotating anode of the tube, which is bombarded by accelerated electrons from a cathode heated by a tungsten filament.

The low-energy X photons are absorbed close to the surface and constitute doses harmful to the skin without being used for the image. The filter is used especially for cutting off the low-energy photons.

In an advantageous embodiment, molybdenum or rhodium-base paths are utilized. These same materials are utilized for the filters.

For dense or thick breasts, it is preferable to use rhodium paths and filters at the X-ray source, for rhodium presents a higher energy peak than molybdenum and therefore makes it possible to obtain more penetrating X-rays. This results in a lower dose delivered to the gland, with a slight loss of contrast. However, the digital detectors used make it possible to compensate for that loss by digital processing.

Thus, a smaller dose is delivered, while having a photon flux at the entrance to the detector which is sufficient to obtain an adequate image. It is altogether possible to have an image with a contrast which can be restored electronically, at a smaller dose (compared to a standard film), for a given compression thickness. If the compression thickness is slightly relaxed, with the same spectrum—rhodium path/rhodium filter—it may be necessary to increase the dose to secure a good image. It is thus possible either to spare the dose or to work at constant dose, in which case the stress on the thickness of the breast can be relaxed.

With the digital technology used according to the preferred embodiment of the invention, the capacity is obtained to make quick acquisitions with the use of suitable electronics. This also permits a kinetic acquisition making it possible to visualize the course of the contrast medium. In that case, image acquisitions are made during the phase of introduction of the contrast medium, those images also being processed by digital subtraction.

Figure 5:
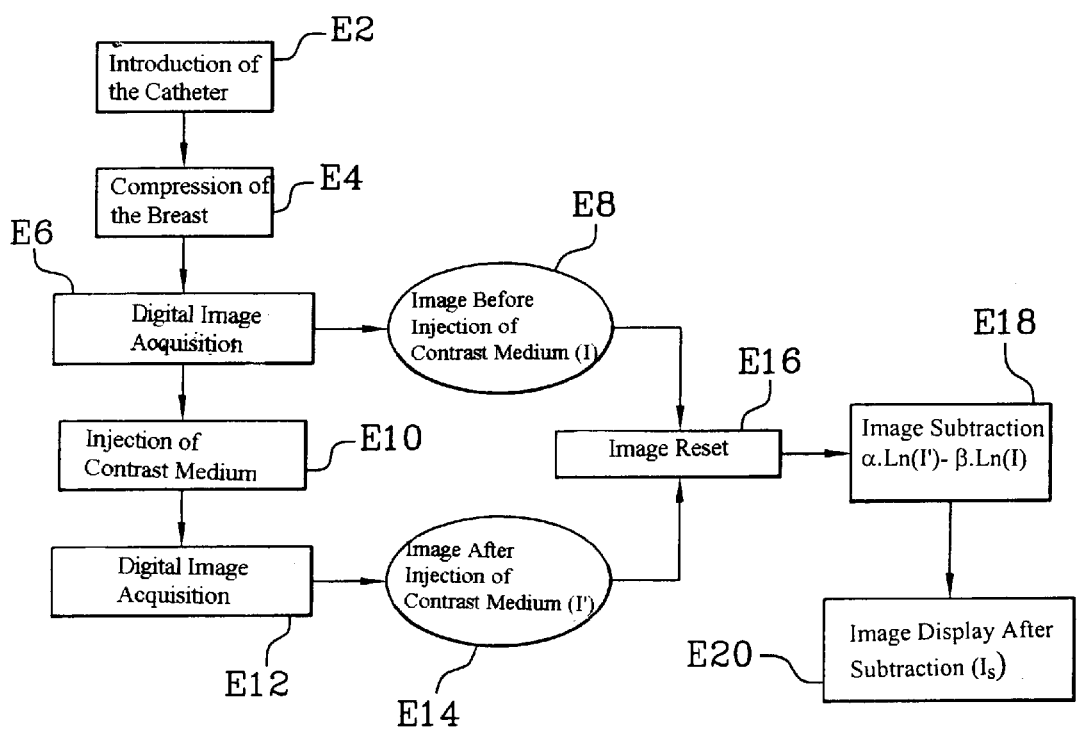
FIG. 5 is a flow chart summarizing the stages of an image subtraction galactography examination of an embodiment of the invention.

FIG. 5 is a flow chart which summarizes the stages of a galactography examination according to the invention. Once the patient's breast is positioned, the catheter 14 is introduced in one of the galactophorous orifices by using the possibilities of displacement of the catheter along axes x, y, z and possibly a polar movement. The catheter is then fixed in injection position by a holding device 38 (stage E2). A compression or an immobilization of the breast is then carried out with the catheter in place (stage E4). A first digital image acquisition is made with the breast compressed or immobilized (stage E6), giving rise to an image before injection of contrast medium (image intensity I) (stage E8). While keeping the breast compressed under the same conditions, the contrast medium is introduced in the galactophorous duct via the catheter 24, which is already in place (stage E10). Once a given quantity of the fluid has been injected, the injection device is closed to prevent a reflux.

The holding device 38 ensures good attachment of the catheter to the breast during that operation. A second digital image acquisition is then made with the breast compressed and the presence of contrast medium (stage E12), giving rise to an image after injection of contrast medium (image intensity I') (stage E14). The compression plate 14 is then lifted to free the breast. The catheter 24 can be withdrawn before or after that release of the breast. The images thus obtained before and after introduction of contrast medium undergo a relative reset, that is, a digital superposition (stage E16). That operation can introduce an image processing with a view to correcting possible movements between the two films. The image subtraction is then made according to the algorithm described above, that is, $\alpha.Ln(I')-\beta.Ln(I)$, with an appropriate choice of coefficients $\alpha$ and $\beta$, depending on the conditions of the examination (stage E18). That operation give rise to image Is, consisting of a matrix of digital pixels. revealing the part of the galactophorous ducts having received the contrast fluid. That image can then be displayed, possible after an adaptation to the display standard provided (stage E20). Of course, it is also possible to perform other operations on the image Is (enhancement of contrast and contours, reformatting, printing on support, remote transmission, etc.).

The invention lends itself to numerous variants possible on both the mechanical and functional levels. Various modifications in structure and/or steps and/or function may be made by one skilled in the art without departing from the scope and extent of the invention as recited in the claims.

What is claimed is:

1. A method of obtaining mammographic images intended for galactography, comprising the following steps:
    a. acquiring a first radiological image of the breast in a compressed or immobilized state:
    b. introducing a contrast medium in a part of the breast;
    c. acquiring at least a second radiological image of the breast in the compressed or immobilized state and with contrast medium; and
    d. partial or complete subtraction of the first image in relation to the second image, or vice versa.

2. The method according to claim 1 wherein the first and second radiological images are obtained by means of a digital X-ray detector.

3. The method according to claim 1 wherein the contrast medium is introduced in at least one galactophorous duct by injection in the nipple via at least one galactophorous orifice.

4. The method according to claim 2 wherein the contrast medium is introduced in at least one galactophorous duct by injection in the nipple via at least one galactophorous orifice.

5. The method according to claim 1 wherein the contrast medium is introduced when the breast is in the compressed or immobilized state.

6. The method according to claim 2 wherein the contrast medium is introduced when the breast is in the compressed or immobilized state.

7. The method according to claim 3 wherein the contrast medium is introduced when the breast is in the compressed or immobilized state.

8. The method according to claim 1 wherein the contrast medium is introduced by a catheter or the like which can be maintained in an adjustable position along at least one of the following axes:
    lateral axis x in the patient's right-left direction;
    lateral axis y in the costal grid-nipple direction; and
    an axis z in the direction of the thickness of the breast.

9. The method according to claim 8 wherein the positioning is adjustable on the set of both lateral axes x and y and axis z.

10. The method according to claim 8 wherein the catheter or the like is further adjustable in polar orientation.

11. The method according to claim 9 wherein the catheter or the like is further adjustable in polar orientation.

12. The method according to claim 1 wherein the movement of the catheter or the like is synchronized along axis z, in the direction of the thickness of the breast, with the movement of compression of the breast.

13. The method according to claim 1 wherein the subtraction is of logarithmic type.

14. The method according to claim 1 wherein a weighting factor is applied to at least one among the first and second images and so as to obtain controlled visibility of the tissues superposed on the opacified parts.

15. The method according to claim 14 wherein at least one of the weighting factors is modified in real time in order to change the relative contrast of the opacified part of the breast and, notably, the galactophorous ducts and neighboring tissues.

16. The method according to claim 1 comprising the acquisition of at least one image during introduction of the contrast medium in order to obtain information concerning the dynamics of progression of the contrast medium in the breast and, notably, in the galactophorous network.

17. The method according claim 1 comprising a stage of resetting of the first and second images before subtraction.

18. The method according to claim 17 wherein the step of image resetting stage applies an "elastic" resetting algorithm.

19. The method according to claim 1 wherein the radiological images are obtained with X-rays presenting a maximum number of photons with an energy around 20 keV in order to favor the contrast of the breast tissues.

20. The method according to claim 1 wherein the radiological images are obtained with X-rays presenting a maximum number of photons with an energy around 35 keV in order to favor the contrast of a contrast medium, for example, of iodinated type.

21. An apparatus for obtaining mammographic images comprising combined in one unit:
   means for maintaining a breast compressed or immobilized; and
   means for holding a catheter or the like for introducing a contrast medium in the breast.

22. Apparatus according to claim 21 comprising means for holding arranged to adjustably position of the catheter or the like along at least one among:
   a lateral axis x in the right-left direction of the patient,
   a lateral axis y in the costal grid-nipple direction, and
   an axis z in the direction of compression of the breast.

23. The apparatus according to claim 22 wherein the means for holding makes possible an adjustable positioning of the catheter or the like on the set of both lateral axes x and y and axis z.

24. The apparatus according to claim 22 wherein the means for holding further include means for adjustment of the catheter or the like in polar orientation.

25. The apparatus according to claim 23 wherein the means for holding further include means for adjustment of the catheter or the like in polar orientation.

26. The apparatus according to claim 21 wherein the means for holding include means for grasping the catheter or the like.

27. The apparatus according to claims 22 wherein the means for holding include means for grasping the catheter or the like.

28. The apparatus according to claims 23 wherein the means for holding include means for grasping the catheter or the like.

29. Apparatus according to claim 26 wherein the means for grasping is guided in direction z of compression of the breast in a block mounted moving on two axes x and y in a lateral plane.

30. The apparatus according to claims 23 wherein for at least one of the axes x, y and z, the means for positioning is adjustable by a motor drive.

31. The apparatus according to claim 21 comprising means for synchronization of movement of the catheter or the like in the direction of compression of the breast with the movement of compression of the breast.

32. The apparatus according to claim 21 comprising means for holding a catheter or the like is configured to make possible the introduction of the latter in a galactophorous orifice of the breast before compression of the breast and to keep the catheter in that orifice during compression of the breast.

33. The apparatus according to claim 21 comprising means for housing a digital X-ray detector positioned directly under the breast.

34. A mammography system comprising an apparatus combined in one unit:
   means for maintaining a breast compressed or immobilized;
   means for holding a catheter or the like for introducing a contrast medium in the breast;
   the apparatus being set up on the axis of emission of an X-ray source a digital X-ray detector;
   means for control; and
   means for processing the images obtained by the latter.

35. The system according to claim 34 comprising means for image processing which includes means for a subtraction of images taken, on the one hand. before and, on the other, during and/or after introduction of the contrast medium.

36. System according to claim 34 wherein the subtraction is of logarithmic type.

37. System according to claim 34 wherein the subtraction is of logarithmic type.

38. A system according to claim 35 wherein the means for image processing means further include means for image resetting used in subtraction.

39. A system according to claim 36 wherein the means for image processing means further include means for image resetting used in subtraction.

40. Use of the system according to claim 34 for digital galactography by image subtraction.

* * * * *